United States Patent [19]

Frick et al.

[11] Patent Number: 5,622,934
[45] Date of Patent: Apr. 22, 1997

[54] PEPTIDES WITH AN INSULIN-LIKE ACTION

[75] Inventors: Wendelin Frick, Frankfur am Main; Günter Müller, Sulzbach am Taunus; Stefan Müllner, Hochheim am Main; Gerhard Breipohl, Frankfurt am Main, all of Germany

[73] Assignee: Hoechst Aktiengesellschaft, Frankfurt am Main, Germany

[21] Appl. No.: 247,394

[22] Filed: May 23, 1994

Related U.S. Application Data

[63] Continuation of Ser. No. 982,902, Nov. 30, 1992.

[30] Foreign Application Priority Data

Nov. 29, 1991 [DE] Germany ............... 41 39 376.7

[51] Int. Cl.$^6$ ............................................. A61K 38/06
[52] U.S. Cl. ................... 514/18; 514/4; 514/7; 514/8; 514/19; 530/331; 530/322
[58] Field of Search ................ 514/18, 19, 7, 514/8, 4; 530/331, 340, 322

[56] References Cited

U.S. PATENT DOCUMENTS

| | | | |
|---|---|---|---|
| 4,212,796 | 7/1980 | Konig | 260/112.5 |
| 4,515,920 | 5/1985 | Erickson | 525/54.11 |
| 4,608,364 | 8/1986 | Grau | 514/4 |
| 4,701,440 | 10/1987 | Grau | 514/3 |
| 4,968,696 | 11/1990 | Stehle | 514/18 |
| 5,302,582 | 4/1994 | Vertesy | 514/23 |
| 5,461,035 | 10/1995 | Mullner | 514/16 |

FOREIGN PATENT DOCUMENTS

| | | |
|---|---|---|
| 89825/91A | 12/1991 | Australia . |
| 2058020 | 6/1992 | Canada . |
| 0132770 | 2/1985 | European Pat. Off. . |
| 0132769 | 2/1985 | European Pat. Off. . |
| 491361 | 6/1992 | European Pat. Off. . |
| 90/09395 | 8/1990 | WIPO . |

OTHER PUBLICATIONS

Lehninger, Albert L., Biochemistry, Ch. 10, pp. 249–252, 1975.
Heyliger et al., "Effect of Vanadate on Elevated Blood Glucose and Depressed Cardiac Performance of Diabetic Rats," Science, 227:1474–1477 (1985).
Shechter et al., "Insulin–like Stimulation of Glucose Oxidation in Rat Adipocytes by Vanadyl (IV) Ions, Nature", 284:556–58 (1980).
Tamura et al., "A Novel Mechanism for the Insulin–like Effect of Vanadate on Glycogen Synthase in Rat Adipocytes," J. Biol. Chem. 259:6650–58.
Mayerovitch et al., "Oral Administration of Vanadate Normalizes Blood Glucose Levels in Streptozoticin–treated Rats," J. Biol. Chem. 262: 6658–62.

Shisheva et al., "Insulinlike Effects of Zinc Ion In Vitro and In Vivo: Preferential Effects on Desensitized Adipocytes and Induction of Normoglycemia in Streptozocin–Induced Rats," Diabetes, vol. 11.
Asplin et al., "Chiro–Inositol Deficiency and Insulin Resistance: A Comparison of the Chiro–inositol–and the Myo–inositol–containing Insulin Mediators Isolated from Urine, Hemodialysate, and Muscle of Control and type II Diabetic Subjects," Proc. Natl. Acad. Sci., 90:5924–5928 (1993).
Ortmeyer et al., "Chiroinositol Deficiency and Insuln Resistance. II. Acute Effects of D–Chiroinositol Administration in Streptozotocin–Diabetic Rats, Normal Rats Given a Glucose Load, and Spontaneously Insulin–Resistant Rhesus Monkeys," Endocrinology, 132:646–651 (1983).
"Insulin Resistance and Noninsulin–Dependent Diabetes Mellitus: Which Horse Is Pulling the Cart?", W. Timothy Garvey, Diabetes/Metabolism Reviews, 5(8):727–742 (1989).
J.A. Maclaren et al., "The Preparation of Reduced and S–Alkylated Wool Keratins Using Tri–n–Butylphosphine," Aust. J. Chem., 19:2355–2360 (1966).
W. Konig et al., "Saure Abspaltung der S–Tritylgruppe am Beispiel synthetischer Insulinfragmente," Liebigs Ann. Chem., 1979, pp. 227–247.
H. Paulsen, "Advances in Selective Chemical Syntheses of Complex Oligosaccharides," Angewandte Chemie, 21(3):155–224 (Mar. 1982).

(List continued on next page.)

*Primary Examiner*—David Lukton
*Attorney, Agent, or Firm*—Finnegan, Henderson, Farabow, Garrett & Dunner, L.L.P.

[57] ABSTRACT

Peptides with an insulin-like action, of formula I:

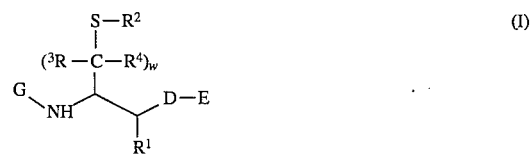

in which G is a hydrogen atom, an amino add residue, or a monosubstituted or polysubstituted amino acid; D is an amino acid residue, a phosphoamino acid residue, a monosaccharide residue, or a covalent bond; E is —NH—$(CH_2)_n$—$NR^5_2$, a glycerol residue, or —NH—$(CH_2)_p$—$R^6$—$R^7$; $R^1$ is $(C_1$–$C_4)$-alkyl or =O; $R^2$ is a sulfhydryl protecting group, $(C_1$–$C_3)$-alkyl, or a hydrogen atom; $R^3$ and $R^4$, independently of one another, are a hydrogen atom or methyl; $R^5$, each being identical or different, is a hydrogen atom, 1 to 6 monosaccharide residues, or 1 to 6 monosubstituted or polysubstituted monosaccharide residues; $R^6$ is O $PO_4H$, $PO_2H$, NHCOO, S or OCOO; $R^7$ is a hydrogen atom, 1 to 6 monosaccharide residues, or 1 to 6 monosubstituted or polysubstituted monosaccharide residues; w is an integer 1 or 2; their preparation and use for treatment of diabetes mellitus or insulin-independent diabetes.

9 Claims, No Drawings

OTHER PUBLICATIONS

R. Schmidt, "New Methods for the Synthesis of Glycosides and Oligosaccharides—Are There Alternatives to the Koenigs–Knorr Method?" Angew. Chem. Int. Ed. Engl., 25:212–235 (1986).

W. Bannwarth et al., "A Simple and Effective Chemical Phosphorylation Procedure for Biomolcules," Helvetica Chimica Acta, 70:175–186 (1987).

C. Murakata et al., "Synthetic Study on Glycophosphatidyl Inositol (GPI) Anchor or *Trypanosoma Brucei:* Glycoheptaosyl Core," Tetrahedron Letters, 31(17):2439–2442 (1990).

A. Finch, "Theilheimer's Synthetic Methods of Organic Chemistry," Yearbook, 45:VIII–XI, XX–XXIII, 6–9 (1991).

PEPTIDES WITH AN INSULIN-LIKE ACTION

This application is a continuation of application Ser. No. 07/982,902 filed Nov. 30, 1992, now abandoned.

The invention relates to peptides with an insulin-like action which are suitable for the treatment of diabetes mellitus.

BACKGROUND OF THE INVENTION

Insulins are made up of two polypeptide chains, the A chain containing 21 amino acid residues and the B chain containing 30 amino acid residues. The A and B chains are bonded to one another via two disulfide bridges, the cysteine residues in positions A7 and B7 and in positions A20 and B19 being linked together. A third disulfide bridge exists between A6 and A11. Animal and human insulins are formed in the pancreata as preproinsulins. Human preproinsulin is made up of a prepeptide containing 24 amino acid residues connected to a proinsulin containing 86 amino acid residues and has the following configuration: prepeptide-B-Arg-Arg-C-Lys-Arg-A, C being an amino acid chain containing 31 residues. During excretion from the Langerhans' islands, the prepeptide is cleaved and proinsulin is formed. Finally the C chain is cleaved by proteolysis and the effective human insulin is formed.

Insulin has many actions on insulin-sensitive tissue. One striking effect is the rapid reduction of the blood glucose level in mammals when insulin is administered. This is caused by a rapid uptake of glucose from the blood by muscle and fat cells. Insulin also activates glycogen synthetase and inhibits lipolysis. Insulin promotes protein synthesis from amino acids, increases the induction of glycokinase and phosphofructokinase and inhibits the formation of certain enzymes of gluconeogenesis, such as pyruvate carboxylase and fructose diphosphatase.

Type II diabetes, or insulin-independent diabetes, is associated with insulin resistance of the peripheral tissues such as muscle or fat tissues. The consequent reduction in glucose utilization is caused by the absence of insulin stimulation of the glucose transport and subsequent metabolic processes. This multiple resistance suggests a defect at receptor or postreceptor level, i.e. before production of the second messenger (Garvey, Diabetes/Metabolism Reviews 5 (1989) 727–742).

Peptides with an insulin-like action have already been disclosed in German patent applications P 40 40 574.5 and P 41 27 495.4.

SUMMARY OF THE INVENTION

In the quest for further effective peptides with an insulin-like action, it has now been found that the peptides according to the invention have an insulin-like action in vitro, a good serum stability and also an insulin-like action on insulin-resistant tissues, and are thus suitable for the treatment of diabetes mellitus.

DETAILED DESCRIPTION OF THE PREFERRED EMBODIMENTS

The invention therefore relates to peptides with an insulin-like action, of formula I:

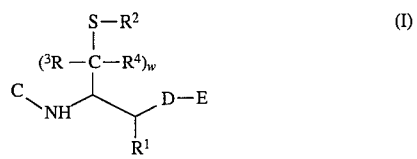

in which

C is:
a) a hydrogen atom,
b) an amino acid residue,
c) an amino acid residue monosubstituted or polysubstituted by:
  1) —CO—$(C_1$–$C_8)$-alkyl, linear or branched, or
  2) an amino acid protecting group, or
d) a sugar residue, D is:
a) an amino acid residue,
b) a phosphoamino acid residue,
c) a sugar residue,
d) a covalent bond, or
e) —OH, E is:
a) a hydrogen atom,
b) —OH,
c) —NH—$(CH_2)_n$—$NR^5_2$, in which $R^5$, which is identical or different, is a radical selected from the group comprising:
  1) a hydrogen atom,
  2) 1 to 6 sugar residues, or
  3) 1 to 6 sugar residues monosubstituted or polysubstituted independently of one another by:
    3.1 methyl,
    3.2 a sugar residue,
    3.3 a disugar residue,

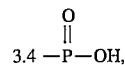

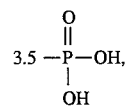

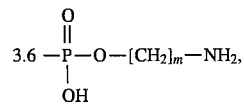

3.7 inositol,
    3.8 inositol phosphate, or
    3.9 a phosphate residue with a phosphate protecting group,
  n is an integer from 0 to 6, and
  m is an integer from 0 to 4,
d) a glycerol residue, or
e) —NH—$(CH_2)_m$—$R_6$—$R^7$, in which $R^6$ is:
  1) —O—,

2) —CO—O—,

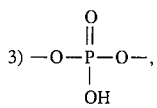

3)

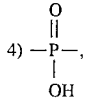

4)

5) —NH—CO—O—,
6) —S—,
7) —SO,
8) —S)$_2$,
9) —SO$_3$, or
10) —O—CO—O—, $R^7$ is:
1) a hydrogen atom,
2) 1 to 6 sugar residues, or
3) 1 to 6 sugar residues monosubstituted or polysubstituted independently of one another by:
 3.1 methyl,
 3.2 a sugar residue,
 3.3 a disugar residue,

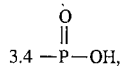

3.4

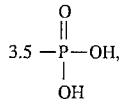

3.5

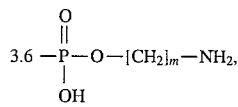

3.6

3.7 inositol,
 3.8 inositol phosphate,
 3.9 a phosphate residue with a phosphate protecting group, or
 3.10 —[CH$_2$]$_m$—CN, and
m is an integer from 0 to 4, $R^1$ is:
 a) —(C$_1$-C$_4$)-alkyl,
 b) =O, or
 c) —O—(C$_1$-C$_4$)-alkyl, $R^2$ is:
 a) a sulfur protecting group,
 b) —SO$_2$,
 c) —SO$_3$,
 d) —(C$_1$-C$_8$)-alkyl,
 e) an O$_3$ radical,

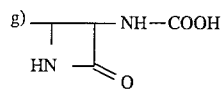

g)

or
 h) a hydrogen atom,
$R^3$ and $R^4$ independently of one another are:
 a) a hydrogen atom, or
 b) methyl, and
W is the integer 1 or 2,
stereoisomeric forms, dimers of the peptides of formula I with cystine as the dimerization component, or physiologically acceptable salts of the peptide of formula I, with the exception of the case where all amino acids of the peptide of formula I are unsubstituted.

Preferred peptides of formula I are those in which C is a residue selected from the group comprising:

an amino acid substituted by acetyl, penicillamine, thiopheneamino acid, Tyr, Asn, Phe, Trp, Nal, D-Tyr, D-Asn or gluconic acid, D is a radical selected from the group comprising: Asp, Asn, D-Asp, D-Asn, Tyr, D-Tyr, —OH, glucosamine or a covalent bond, E is:
 a) a hydrogen atom,
 b) —NH—(CH$_2$)$_n$—NR$^5{}_2$, in which R$^5$, which is identical or different, is a radical selected from the group comprising:
  1) a hydrogen atom,
  2) glucose,
  3) gluconic acid,
  4) galactonic acid,
  5) mannonic acid,
  6) glucosamine,
  7) mannose,
  8) fructose,
  9) galactose,
  10) dimannose, or
  11) trimannose, and
 n is an integer from 0 to 4, or
 c) —NH—(CH$_2$)$_m$—R$_6$—R$^7$, in which R$^6$ is:
  1) —O—,
  2) —O—CO—O—,

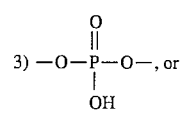

3)             , or

4) —NH—CO—O—, $R^7$ is:
 1) a hydrogen atom, or
 2) de fined as under b)1) to b)11), and
 m is an integer from 1 to 3, $R^1$ is:
 a) =O, or
 b) methyl, $R^2$ is:
 a) a hydrogen atom,
 b) methyl, or
 c) —SO$_3$, and W is the integer 1 or 2,
stereoisomeric forms or physiologically acceptable salts of the peptide of formula I.

Especially preferred peptides of formula I are those in which

C is a residue selected from the group comprising Tyr, D-Tyr or Asn,

D is a residue selected from the group comprising Asn, D-Asn or a covalent bond, E is:
 a) ethylenediamine, or
 b) —NH—(CH$_2$)$_m$—R$^6$—R$^7$, in which R$^6$ is:

1) —O—, or

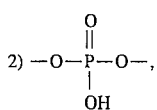

and R⁷ is:
1) a hydrogen atom,
2) mannose, or
3) mannose monosubstituted to tetrasubstituted independently of one another by:
   3.1 methyl,
   3.2 mannose,
   3.3 dimannose,
   3.4 galactose, or
   3.5 digalactose,
$R^1$ is =O,
$R^2$, $R^3$ and $R^4$ are all hydrogen atoms, and
W is 1,
stereoisomeric forms or physiologically acceptable salts of the peptide of formula I.

Particularly preferred peptides of formula I are those in which
C is a residue selected from the group comprising Tyr, Asn, D-Tyr, D-Asn, 2-(thien-2-yl)glycine, 3-(thien-2-yl)alanine or Phe,
D is a residue selected from the group comprising Asn, Tyr, D-Asn or D-Tyr,
E is a hydrogen atom, ethylenediamine or ethanolamine,
W is 1 or 2,
$R^1$ is =O, and
$R^2$ is a hydrogen atom or methyl,
stereoisomeric forms or physiologically acceptable salts of the peptide of formula I.

The term alkyl is understood as meaning linear or branched hydrocarbon chains.

The terms amino acids and amino acid residues are understood as meaning e.g. the stereoisomeric forms, i.e. D or L forms, of the following compounds: alanine glycine proline alanine
cysteine
aspartic acid
glutamic acid
phenylalanine
tryptophan
glycine
histidine
isoleucine
lysine
leucine
methionine
asparagine
proline
glutamine
arginine
serine
threonine
valine
2-aminoadipic acid
3-aminoadipic acid
beta-alanine
2-aminobutyric acid
4-aminobutyric acid
piperidic acid
6-aminocaproic acid
2-aminoheptanoic acid
2-(thien-2-yl)glycine
penicillamine
n-ethylasparagine
hydroxylasparagine
allo-hydroxylysine
3-hydroxyproline
4-hydroxyproline
isodesmosine
allo-isoleucine
N-methylglycine
2-aminoisobutyric acid
3-aminoisobutyric acid
2aminopimelic acid
2,4-diaminobutyric acid
desmosine
2,2-diaminopimelic acid
2,3-diaminopropionic acid
N-ethylglycine
3-(thien-2-yl)alanine
sarcosine
N-methylisoleucine
6-N-methyllysine
N-methylvaline
norvaline
norleucine
ornithine The shorthand versions used for the amino acids are in accordance with the generally conventional versions (cf. Schröder, Lübke, The Peptides, volume I, New York 1965, pages XXII–XXIII; Houben-Weyl, Methoden der Organischen Chemie (Methods of Organic Chemistry), volume XV/1 and 2, Stuttgart 1974). The amino acid pGlu represents pyroglutamyl, Nal represents 3-(naphth-2-yl)alanine, Aza-gly—$NH_2$ represents a compound of the formula $NH_2$—NH—$CONH_2$ and D-Asp represents the D form of aspartic acid. The term phosphoamino acids is understood as meaning amino acids in which the carboxyl group has been replaced with a phosphate group. By their chemical nature, peptides are acid amides and decompose to amino acids on hydrolysis. The bond between C—where it is an amino acid—and the compound of formula II:

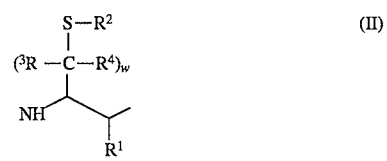

in which $R^1$, $R^2$, $R^3$, $R^4$ and W are as defined in formula I, is a peptide bond. The bonds between
a) D and E,
b) D and the compound of formula II, or
c) E and the compound of formula II, where D and E are amino acids or amino acid residues, are all peptide bonds. This also applies to the case where E is an amine derivative, as described under E c) or E e).

Sugars are understood as meaning aldoses and ketoses having 3 to 7 carbon atoms, which can belong to the D or L series; these also include amino sugars or uronic acids. Examples which may be mentioned are glucose, mannose, fructose, galactose, ribose, erythrose, glyceraldehyde, sedoheptulose, glucosamine, galactosamine, glucuronic acid, galacturonic acid, gluconic acid, galactonic acid or mannonic acid. Disugars are understood as meaning saccharides made up of two sugar units.

Di-, tri- or oligosaccharides are formed by the acetal-type bonding of 2 or more sugars, it being possible for the bonds to be in the α or β form. The bonds between the sugars are preferably formed via carbon atom 1 and carbon atom 6, carbon atom 1 and carbon atom 2 or carbon atom 1 and carbon atom 4 of the sugars in question. The α form of the bond between the sugars is preferred.

If the sugar is substituted, the substitution preferably takes place on the hydrogen atom of an OH group of the sugar.

The compounds according to the invention can contain one or more phosphate groups, which can also be derivatized with a phosphate protecting group.

Examples of phosphate protecting groups are phenyl, benzyl or hydroxypropylnitrile (Houben-Weyl, Methoden der Organischen Chemie (Methods of Organic Chemistry), volume 12/1 or volume 12/2; Teiheimer, Synthetic Methods of Organic Chemistry, vol. 45).

The term insulin-resistant tissue is understood as meaning for example rat fat cells which no longer possess an insulin receptor.

Physiologically acceptable salts of the compound of formula I are to be understood in particular as meaning pharmaceutically applicable or non-toxic salts. Such salts are formed e.g. by compounds of formula I containing acid groups, e.g. carboxyl, with alkali metals or alkaline earth metals, e.g. Na, K, Mg and Ca, and with physiologically acceptable organic amines, e.g. triethylamine and tris(2-hydroxyethyl)amine. Compounds of formula I containing basic groups, e.g. an amino group or a guanidino group, form salts with inorganic acids, e.g. hydrochloric acid, sulfuric acid or phosphoric acid, and with organic carboxylic or sulfonic acids, e.g. acetic acid, citric acid, benzoic acid, maleic acid, fumaric acid, tartaric acid and p-toluenesulfonic acid. Compounds containing an equal number of basic and acid groups form internal salts and do not need a third salt component.

The invention further relates to a process for the preparation of peptides of formula I, wherein
  a) a segment containing a free carbon-terminal carboxyl group, or an activated derivative thereof, is reacted with an appropriate segment containing a free nitrogen-terminal amino group, or
  b) the peptide is synthesized in stages,
if appropriate, one or more protecting groups temporarily introduced for the protection of other functional groups are cleaved in the compound obtained according to (a) or (b), and, if desired, the resulting compound of formula I is converted to its physiologically acceptable salt.

The peptides according to the invention are prepared by the general methods of peptide chemistry, either in stages from the carbon-terminal end or by the coupling of segments (Houben-Weyl, Methoden der Organischen Chemie (Methods of Organic Chemistry), volume 15/1,2). The peptides can be coupled e.g. by the mixed anhydride method, via active esters or azides or by the carbodiimide method, especially with the addition of substances for accelerating the reaction and preventing racemization, e.g. 1-hydroxy-benzotriazole, N-hydroxy-succinimide, 3-hydroxy-4-oxo-3,4-dihydro-1,2,3-benzo-triazine or N-hydroxy-5-norbornene-2,3-dicarboximide, and also using active derivatives of 1-hydroxybenzotriazole or anhydrides of phosphoric, phosphonic and phosphinic acids, at a reaction temperature of between −10° C. and the boiling point of the solvent, preferably of between −5° C. and 40° C.

Suitable solvents for this purpose are dimethylformamide, dimethylacetamide, N-methylpyrrolidone or dimethyl sulfoxide. If the solubility of the components allows it, it is also possible to use solvents such as methylene chloride, chloroform or tetrahydrofuran. Said methods are described e.g. in Meinhofer-Gross: "The Peptides", Academic Press, vol. 1 (1979).

If it is necessary for the prevention of secondary reactions or for the synthesis of special peptides, the functional groups in the side-chain of amino acids are additionally protected by suitable protecting groups (see e.g. T. W. Greene, "Protective Groups in Organic Synthesis"), Arg(Tos), Arg(Mts), Arg(Mtr), Arg(PMV), Asp(OBzl), Asp(OBut), Cys(4-Me-Bzl), Cys(Acm), Cys(SBut), Glu(OBzl), Glu(OBut), His-(Tos), His(Fmoc), His(Dnp), His(Trt), Lys(Cl-Z), Lys(Boc), Met(O), Ser(Bzl), Ser(But), Thr(Bzl), Thr(But), Trp(Mts), Trp(CHO), Tyr(Br-Z), Tyr(Bzl) or Tyr(But) being used primarily.

Preferred amino protecting groups are the benzyloxycarbonyl (Z) radical, which can be cleaved by catalytic hydrogenation, the 2-(3,5-dimethoxyphenyl)prop-2-yloxycarbonyl (Ddz) or trityl (Trt) radical, which can be cleaved with weak acids, and the 9-fluorenylmethoxy-carbonyl (Fmoc) radical, which can be cleaved with secondary amines. The SH group of cysteine can be blocked by a number of protecting groups, the trityl (Trt) radical and the S-tert-butyl (StBu) radical being preferred here. The trityl radical can be cleaved by oxidation with iodine to form the cystine compounds or by reductive acid cleavage to form the cysteine compounds (Liebigs Ann. Chem. 1979, 227–247).

The S-tert-butyl radical, on the other hand, is best cleaved reductively with tributylphosphine (Aust. J. Chem. 19 (1966) 2355–2360). OH and COOH functional groups in the side-chains are best protected by the tert-butyl (tBu) radical, which can be cleaved with acid (see also: Meienhofer-Gross: "The Peptides", vol. 3).

The oligosaccharides are prepared by known processes (H. Paulsen, Angew. Chem. Int. Ed. 21 (1982) p. 155). It is preferable to use the trichloroacetimidate method of synthesizing oligosaccharides (R. R. Schmidt, Angew. Chem. Int. Ed. 25 (1986) 212–235; T. Ogawa, Tetrahedron Lett. 31 (1990) 2439–2442).

The phosphates are synthesized by means of the phosphite triester method (W. Bannwarth, Helv. Chim. Acta 70 (1987) 175–186); the first reaction step is preferably carried out with the peptide part of the peptide of formula I and the second reaction step with the oligosaccharide part.

Mainly the following protecting groups are possible for the hydroxyl groups of the sugars: benzyl, acetyl, benzoyl, pivaloyl, trityl, tert-butyldimethylsilyl, benzylidene or isopropylidene protecting groups.

The compounds of formula I and their physiologically acceptable salts are used primarily as active ingredients in pharmaceutical formulations for the treatment of diabetes mellitus or insulin-independent diabetes.

The invention therefore further relates to a pharmaceutical formulation which contains at least one compound of formula I and/or at least one of its physiologically acceptable salts in dissolved, amorphous and/or crystalline form—preferably in amorphous and/or crystalline form.

The pharmaceutical formulation is preferably an injectable solution or suspension with a pH of about 3.0 to 9.0, preferably of about 5.0 to 8.5, which contains a suitable isotonic agent, a suitable preservative and, if appropriate, a suitable buffer, and also, if appropriate, a depot principle, all in sterile aqueous solution or suspension. All the constituents of the formulation, except the active ingredient, make up the excipient of the formulation.

Examples of suitable isotonic agents are glycerol, glucose, mannitol, NaCl and calcium or magnesium compounds, e.g. $CaCl_2$ or $MgCl_2$.

Examples of suitable preservatives are phenol, m-cresol, benzyl alcohol and/or p-hydroxybenzoic acid esters.

Examples of buffer substances which can be used, especially for adjusting the pH to about 5.0 to 8.5, are sodium acetate, sodium citrate or sodium phosphate. Other substances which are also suitable for adjusting the pH are physiologically acceptable dilute acids (typically HCl) or alkaline solutions (typically NaOH).

To vary the action profile of the formulation according to the invention, it is also possible to admix modified insulins (cf. European patent application B 132 769 and European patent application B 132 770) and/or unmodified insulins, preferably bovine, porcine or human insulin and especially human insulin.

The pharmaceutical formulation is prepared by converting at least one compound of formula I and/or at least one of its physiologically acceptable salts to a suitable form of administration, if appropriate together with modified and/or unmodified insulins (insulin derivatives), with a physiologically acceptable excipient and, if appropriate, with suitable additives and adjuncts.

EXAMPLES

The invention will now be illustrated in greater detail by means of the following Examples.

Example 1

H-L-Tyr-L-Cys-L-Asn-NH—$CH_2$—$CH_2$OH

1a) Z-Asn-NH—$CH_2$—$CH_2$—OAc (2):

8.0 g (20.6 mmol) of Z-AsnONp 1 are dissolved in 200 ml of pyridine, and 5 g (81.8 mmol) of ethanolamine and 5 ml of N-ethylmorpholine are added. After standing for 16 hours at room temperature, 50 ml of acetic anhydride are added dropwise at 5° C., with stirring. The reaction mixture is stirred for a further 2 hours at room temperature and then concentrated under high vacuum. The residue is dissolved in 150 ml of hot methanol and the solution is concentrated. The product crystallizes after the addition of 100 ml of methylene chloride/methanol (15:1) and 200 ml of n-heptane/ethyl acetate (2:1). The yield is 6.1 g (84%) of white crystals of m.p. 175° C. TLC [methylene chloride/methanol (9:1)] $R_f=0.7$. $C_6H_2N_3O_6$ (351.36).

1b) H-Asn-NH—$CH_2$—$CH_2$—OAc (3):

2.0 g of palladium-on-charcoal (10% Pd) are added to a solution of 12.0 g (34.0 mmol) of 2 in 200 ml of methanol/acetic acid (1:1) and the mixture is hydrogenated for 2 hours at room temperature. The solution is filtered on silica gel and concentrated and the residue is purified by flash chromatography [methylene chloride/methanol/concentrated ammonia (30/5/1)]. Yield 7.3 g (98%) of a yellowish oil. TLC [methylene chloride/methanol/concentrated ammonia (30/5/1)] $R_f=0.5$. $C_8H_{15}N_3O_4$ (217.23).

1C) Trt-Cys-(Trt)-Asn-NH—$CH_2$—$CH_2$—OAc (4):

1.5 g (4.5 mmol) of TOTU1 [o-(cyano(ethoxycarbonyl)methylidene)amino-1,1,3,3-tetramethyluronium tetrafluoroborate], 0.64 g (4.5 mmol) of oxime [ethyl(hydroxyimino)cyanoacetate] and 1.7 ml (13.5 mmol) of N-ethylmorpholine are added at 0° C., with stirring, to a solution of 0.8 g (3.7 mmol) of 3 and 2.8 g (4.5mmol) of Trt-Cys-(Trt)-OH in DMF and the mixture is stirred for 2 hours at 0° C. After the addition of 200 ml of ethyl acetate, the mixture is washed 3 times with saturated $NaHCO_3$ solution, dried over $MgSO_4$ and concentrated. The residue is triturated with n-heptane/ethyl acetate (6:1). Yield 2.2 g (74%) of white crystals. M.p. 185° C. TLC [methylene chloride/methanol (15:1)] $R_f=0.4$. $C_{49}H_{48}N_4O_5S$ (805.0).

1d) H-Cys-(Trt)-Asn-NH—$CH_2$—$CH_2$OH (5):

4.0 g (5.0 mmol) of 4 are dissolved in 200 ml of $CH_2Cl_{12}$. 4 ml of water and 3 ml of trifluoroacetic acid are added. After 15 minutes, the mixture is washed 3 times with saturated $NaHCO_3$ solution, dried over $MgSO_4$ and concentrated. The residue is dissolved in 50 ml of absolute methanol, and 0.5 ml of 1M sodium methanolate solution is added dropwise. After 15 minutes, 50 ml of methylene chloride are added and the mixture is filtered on silica gel. After concentration of the solvent, the residue is purified by flash chromatography [methylene chloride/methanol (9:1)]. Yield 2.2 g (85%) of a white amorphous solid. TLC [methylene chloride/methanol (5:1)] $R_f=0.7$. $C_{28}H_{32}N_4O_4S$ (520.6).

1e) Boc-Tyr-(Boc)-Cys-(Trt)-Asn-NH—$CH_2$—$CH_2$OH (6):

2.2 g (4.2 mmol) of 5, 2.1 g (5.5 mmol) of Boc-Tyr-(Boc)-OH, 1.8 g (5.5 mmol) of TOTU, 0.8 g (5.5 mmol) of oxime and 1.4 ml (11 mmol) of N-ethylmorpholine are reacted analogously to the preparation of 4. Yield 2.6 g (70%) of white crystals. M.p. 169°–170° C. TLC [methylene chloride/methanol (15:9)] $R_f=0.3$. $C_{47}H_{57}N_5O_{10}S$ (884.07).

1f) H-Tyr-Cys-Asn-NH—$CH_2$—$CH_2$OH (7):

2.0 g (2.3 mmol) of 6 are dissolved in a mixture of 10 ml of trifluoroacetic acid and 10 ml of ethylmercaptan. After 4 hours, the reaction mixture is poured into 100 ml of water. The aqueous phase is extracted 3 times with ether and the aqueous phase is concentrated. The residue is purified by flash chromatography [methylene chloride/methanol/concentrated ammonia (30/15/5)]. Yield 0.85 g (85%). TLC [methylenechloride/methanol/concentrated ammonia (30/15/5)] $R_f=0.3$. $C_{18}H_{27}N_5O_6S$ (441.51). MS $(M+H^+)=442.5$.

Example 14

H-Tyr-Cys-AsnNH—$CH_2$—$CH_2$—O—PO(OH)-O-6Man$\alpha$1-OMe

14a) Trt-Cys-(Trt)-AsnNH—$CH_2$—$CH_2$-O-PO(O—$CH_2$—$CH_2$—CN)-O-6Man(2,3,4-tribenzyl)$\alpha$1-OMe (8) (Me is a methyl radical, Man is a mannose residue)

1.1 g (2.37 mmol) of methyl-2,3,4-tri-O-benzyl-$\alpha$-D-mannopyranoside (A. Vasella, Helv. Chim. Acta 62 (1979) 2400–2410) are dissolved in 15 ml of dry acetonitrile. 1.36 g (4.50 mmol) of bis(diisopropylamino)(2-cyanoethoxy)phosphine (Aldrich) and 170 mg (2.40 mmol) of tetrazole (recrystallized twice from ethyl acetate) are added. After 20 minutes, the mixture is filtered on a small amount of silica gel with n-heptane/ethyl acetate (2:1) and the filtrate is concentrated.

The oily residue (2.0 g) is dissolved in 10 ml of dry acetonitrile and 8 ml of dry methylene chloride and a solution of 1.5 g (1.97mmol) of Trt-Cys-(Trt)-AsnNH- CH$_2$—CH$_2$—OH in 5 ml of dry tetrahydrofuran is added. After the addition of 175 mg (2.5 mmol) of tetrazole, the solution is left to stand for 2 hours at room temperature. It is then filtered on a small amount of silica gel with methylene chloride/methanol (15:1) and the filtrate is concentrated (3 g of crude product).

The crude product is dissolved in 50 ml of methylene chloride and cooled to 0° C. After the addition of 500 mg of metachloroperbenzoic acid, the mixture is stirred for 20 minutes at 20° C., diluted with 200 ml of methylene chloride and washed 3 times with saturated NaHCO$_3$ solution. The organic phase is dried over MgSO$_4$, filtered and concentrated and the residue is purified by flash chromatography [methylene chloride/methanol (15:1)]. Yield 1.2 g (45% over 3 stages). Thin layer chromatography (TLC) [methylene chloride/methanol (15:1)] R$_f$=0.3. C$_{78}$H$_{80}$N$_5$O$_{12}$PS (1342.61). MS (M+Li$^+$)=1348.4.

4b)    H-Cys-(Trt)-Asn-NH—CH$_2$—CH$_2$—O—PO(O—CH$_2$—CH$_2$—CN)-O-6Man(2,3,4-tribenzyl)α1-OMe (9)

1.2 g (0.89 mmol) of 8 are dissolved in 70 ml of methylene chloride. 1 ml of water and 1 ml of trifluoroacetic acid are added. After 15 min, the mixture is washed 3 times with saturated NaHCO$_3$ solution, dried over MgSO$_4$ and concentrated. The residue is purified by flash chromatography [methylene chloride/methanol (15:1)]. Yield 0.79 g (80%). TLC [methylene chloride/methanol (9:1)] R$_f$=0.60. C$_{59}$H$_{66}$N$_5$O$_{12}$PS (1100.28). MS (M+Li$^+$)=1106.4.

14c)    Z-Tyr-(Bn)-Cys-(Trt)-AsnNH—CH$_2$—CH$_2$—O—PO(O—CH$_2$—CH$_2$—CN)-O-6Man(2,3,4-tribenzyl)-α1-OMe (10)

300 mg (0.27 mmol) of 9, 325 mg (0.80 mmol) of Z-Tyr-(Bn)-OH (Bachem), 260 mg (0.80 mmol) of TOTU, 115 mg (0.80 mmol) of oxime and 0.3 ml (2.5 mmol) of N-ethyl-morpholine are reacted analogously to the preparation of 4 (Example 1c)). Yield 320 mg (79%) of a white solid. TLC [methylene chloride/methanol (9:1)] R$_f$=0.65.

14d)    H-Tyr-Cys-AsnNH—CH$_2$—CH$_2$—O—PO(OH)-O-6Manα1-OMe (11)

40 ml of ammonia are liquefied at −78° C. and 100 mg of sodium are added. After stirring for 15 minutes, 20 ml of dry tetrahydrofuran (THF) are added. A solution of 120 mg (0.080 mmol) of 10 in 10 ml of dry THF is then added dropwise. The solution is stirred at −78° C. for 30 minutes. It is worked up by the addition of ammonium chloride until the blue color disappears. 20 ml of methanol and 10 ml of water are then added cautiously. The solution is concentrated and the residue is purified by flash chromatography [methylene chloride/methanol/concentrated ammonia (3:3:1)]. Yield 40 mg (71%) of a white solid. TLC [methylene chloride/ methanol/concentrated ammonia (3:3:1)] R$_f$=0.2–0.3. C$_{25}$H$_{40}$N$_5$O$_{14}$PS (697.68). MS (M+H$^+$)=698.3.

The following compounds are prepared according to the reaction steps of Example 1 or 14:

TABLE 1

| Example No. | Compound | Empirical formula Molecular weight | Mass spectrum Mol peak (M + H$^+$) |
|---|---|---|---|
| 1 | H—L—Tyr—L—Cys—L—Asn—NH—CH$_2$—CH$_2$—OH | C$_{18}$H$_{27}$N$_5$O$_6$S 441.5 | 442.5 |
| 2 | H—L—Tyr—L—Cys—NH—CH$_2$—CH$_2$—NH$_2$ | C$_{14}$H$_{22}$N$_4$O$_3$S 326.4 | 327.4 |
| 3 | H—L—Asn—L—Cys—L—Tyr—NH—CH$_2$—CH$_2$OH | C$_{18}$H$_{27}$N$_5$O$_6$S 441.5 | 442.5 |
| 4 | H—D—Tyr—L—Cys—L—Asn—NH—CH$_2$—CH$_2$OH | C$_{18}$H$_{27}$N$_5$O$_6$S 441.5 | 442.5 |
| 5 | H—L—Cys—L—Asn—NH—CH$_2$—CH$_2$OH | C$_9$H$_{18}$N$_5$O$_6$S 278.3 | 279.3 |
| 6 | H—L—Cys—L—Tyr—NH—CH$_2$—CH$_2$OH | C$_{14}$H$_{21}$N$_3$O$_4$S 327.4 | 328.4 |
| 7 | H—L—Tyr—L—Cys—NH—(CH$_2$)$_4$—NH$_2$ | C$_{16}$H$_{26}$N$_4$O$_3$S 354.5 | 355.5 |
| 8 | H—(3—(thien—2—yl)—L—Ala)—L—Cys—L—Asn—OH | C$_{14}$H$_{20}$N$_4$O$_5$S 388.5 | 389.5 |
| 9 | H—L—Tyr—L—Cys—L—Asn—NH—CH$_2$—CH$_2$—NH—gluconic acid | C$_{24}$H$_{38}$N$_6$O$_{11}$S 618.7 | 619.7 |
| 10 | H—L—Tyr—L—Cys—L—Asn—NH—CH$_2$—CH$_2$—NH$_2$ | C$_{18}$H$_{28}$N$_6$O$_5$S 440.5 | 441.5 |
| 11 | Acetyl—L—Tyr—L—Cys—L—Asn—NH—CH$_2$—CH$_2$OH | C$_{20}$H$_{29}$N$_5$O$_7$S 483.6 | 484.6 |
| 12 | H—L—Tyr—L—Cys—L—Asn—OH | C$_{16}$H$_{22}$N$_4$O$_6$S 398.5 | 399.5 |
| 13 | H—L—Tyr—L—Cys—L—Asn—NH—(CH$_2$)$_2$—O—PO(OH)—O(CH$_2$)$_2$—CN | C$_{21}$H$_{31}$N$_6$O$_9$PS 591.2 | 575.2 |
| 14 | H—L—Tyr—L—Cys—L—Asn—NH—(CH$_2$)$_2$—O—PO(OH)—O—6Manα1—O—CH$_3$ | C$_{25}$H$_{40}$N$_5$O$_{14}$PS 697.6 | 698.3 |
| 15 | H—L—Tyr—L—Cys—L—Asn—NH—(CH$_2$)$_2$—O—PO(OH)—O—6Manα1—2Manα1—O—CH$_3$ | C$_{31}$H$_{50}$N$_5$O$_{19}$PS 859.3 | 860.3 |
| 16 | L—Tyr—L—Cys—L—Asn—NH—(CH$_2$)$_2$—O—PO(OH)—O—6Manα1—2—Manα1—6Manα1—O—CH$_3$ | C$_{37}$H$_{60}$N$_5$O$_{24}$PS 1021.7 | 1022.7 |

Man represents the sugar mannose in Table 1.

The biological activity of the peptides of formula I according to the invention is determined with the aid of preparatively isolated rat fat cells and diaphragm fragments.

Rat fat cells were prepared as follows: Fatty tissue of the epididymis (Wistar rat, 160–180 g, no feed restriction) is digested with collagenase and the resulting isolated fat cells are washed several times by flotation.

Preparation of rat diaphragm fragments: Small tissue fragments (5 mm diameter) are punched out of hemidiaphragms (Wistar rat, 60–70 g, no feed restriction) which have been washed several times.

A) Glycogenesis

This test determines the insulin-stimulatable glycogen synthesis in muscle cells, comprising the glucose transport via the plasma membrane and the conversion of the glucose to glycogen, including the functional insulin signal transmission cascade.

Diaphragm fragments are incubated for 15 min at 37° C. in Krebs-Ringer-Henseleit buffer (KRH buffer) with 50 μM D-[U-$^{14}$C]glucose in the presence or absence of insulin or the peptides according to the invention. After the medium has been filtered with suction, the tissue fragments are intensively washed, frozen at −70° C. and then homogenized at 2° C. in a Polytron pulverizer. The homogenate is centrifuged (2000 g) and the supernatant is pipetted onto filter paper. To determine the glycogen formed, the filters are transferred into trichloroacetic acid (TCA) (5%), washed with ethanol and acetone and dried and their radioactivity is determined via scintillation measurement ([$^{14}$C]glycogen [dpm×10$^{-3}$]).

B) Lipogenesis

This test determines the insulin-stimulatable conversion of glucose to toluene-soluble products (triglycerides, phospholipids, fatty acids), requiring the glucose transport and the triglyceride (glycerol-3-P synthesis, esterification)/phospholipid/fatty acid synthesis, including the insulin signal transmission cascade.

Rat fat cells in KRH buffer are incubated for 90 min at 37° C. with D-[3-$^3$H]glucose (0.2 mM or 1 mM final concentration) in the presence or absence of insulin or peptides according to the invention. By the addition of a toluene-soluble scintillation cocktail, the cells are digested and the lipids separated from water-soluble products and the incubation medium. After phase separation, the radioactivity incorporated into lipids is determined by scintillation measurement directly without removal of the aqueous phase ([$^3$H]lipid [dpm×10$^{-3}$]).

C) Glucose transport activity

Isolated plasma membrane vesicles are obtained from rat fat cells by washing the fat cells twice in homogenization buffer (20 mM trihydroxyaminomethane (Tris)/HCl, pH 7.4, 1 mM, 4° C., EDTA, 0.25M sucrose) and then homogenizing them in 20 ml of the same buffer (glass homogenizer with Teflon pestle).

The homogenate is centrifuged (16,000×g, 15 min) and the sediment is suspended in the same buffer and centrifuged again. The sediment is suspended in 5 ml of homogenization buffer and layered onto a sucrose cushion (1.12M sucrose, 20 mM Tris/HCl, pH 7.4, 1 mM EDTA); after centrifugation (100,000×g, 70 min), the interphase containing the plasma membrane vesicles is removed with a syringe, diluted with 45 ml of buffer and centrifuged again (48,000×g, 45 min). The sediment is suspended in 10 ml of buffer, centrifuged again and resuspended in 3 ml of buffer.

Isolated plasma membrane vesicles are incubated for 30 min at 25° C. in the presence or absence of insulin or the peptides according to the invention. The vesicles are then incubated for 10 sec at 25° C. with 50 μM D-[3-$^3$H]glucose and L-[1-$^4$C]glucose of the same specific radioactivity. The mixtures are rapidly filtered with suction on nitrocellulose filters. The filters are washed copiously and dried. Their radioactivity is determined by liquid scintillation measurement. The specific transport (D-[$^3$H]glucose/L-[$^4$C]glucose [dpm×10$^{-3}$]) is calculated as the difference between the [$^3$H] and [$^{14}$C] radioactivity.

Table 2 shows the results in percent of the maximum insulin action. The action of human insulin (HI) is given a value of 100%. The concentration data of the peptides according to the invention used are based on the concentration at which 25% or 20% of the maximum HI action is reached.

TABLE 2

| Compound Example no. | Lipogenesis % of the max. HI action | Concentration [μM] at which 25% of the max. HI action is reached | Glucose transport % of the max. HI action | Concentration [μM] at which 20% of the max. HI action is reached | Glycogenesis % of the max. HI action | Concentration [μM] at which 25% of the max. HI action is reached |
|---|---|---|---|---|---|---|
| 1 | 35 | 375 | 42 | 240 | 26 | 550 |
| 2 | 32 | 500 | 40 | 350 | 28 | 650 |
| 3 | 31 | 375 | 38 | 225 | 42 | 285 |
| 4 | 31 | 410 | 38 | 260 | 23 | — |
| 5 | 21 | — | 25 | 600 | 16 | — |
| 6 | 17 | — | 24 | 750 | 32 | 480 |
| 7 | 18 | — | 10 | — | 2 | — |
| 8 | 26 | 450 | 25 | 410 | 31 | 375 |
| 9 | 12 | — | 15 | — | 11 | — |
| 10 | 30 | 330 | 42 | 300 | 25 | 450 |
| 11 | 36 | 200 | 40 | 260 | 45 | 240 |
| 12 | 26 | 750 | 20 | 880 | 15 | — |
| 13 | 33 | 120 | 36 | 140 | 31 | 100 |
| 14 | 37 | 95 | 40 | 105 | 32 | 90 |
| 15 | 35 | 142 | 32 | 122 | 29 | 139 |
| 16 | 24 | 125 | 29 | 152 | 25 | 135 |

What is claimed is:

1. A peptide of formula I:

 (I)

in which

G is:
a) a hydrogen atom,
b) an amino acid residue, or
c) an amino acid residue monosubstituted or polysubstituted by:
1) —CO—($C_1$–$C_8$)-alkyl, linear or branched, or
2) an amino acid protecting group, D is:
a) an amino acid residue,
b) a phosphoamino acid residue,
c) a monosaccharide residue, or
d) a covalent bond, E is:
a) —NH—$(CH_2)_n$—$NR^5_2$, in which each $R^5$ is identical or different and is a moiety selected from the group consisting of
1) a hydrogen atom,
2) 1 to 6 monosaccharide residues, and
3) 1 to 6 monosaccharide residues monosubstituted or polysubstituted independently of one another by:
3.1 methyl,
3.2 a monosaccharide residue,
3.3 a disaccharide residue,

 3.4

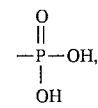 3.5

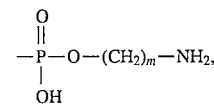 3.6

3.7 inositol,
3.8 inositol phosphate, or
3.9 a phosphate group bearing a phenyl, benzyl, or propylnitrile moiety,
n is an integer from 0 to 6, except
n cannot be 1 when $R^5$ is hydrogen, and
m is an integer from 0 to 4,
b) a glycerol residue, or
c) —NH—$(CH_2)_p$—$R^6$—$R^7$, in which p is 2 to 4, $R^6$ is :
1) —O—, 2) 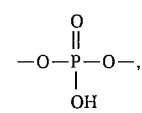

3) ,

4) —NH—CO—O—,
5) —S— or
6) —O—CO—O—, $R^7$ is:
1) a hydrogen atom,
2) 1 to 6 monosaccharide residues, or
3) 1 to 6 monosaccharide residues monosubstituted or polysubstituted independently of one another by:
3.1 methyl,
3.2 a monosaccharide residue,
3.3 a disaccharide residue,

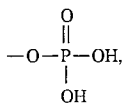 3.4

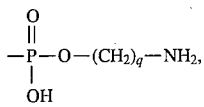 3.5

3.6

$$-\underset{\underset{OH}{|}}{\overset{\overset{O}{\|}}{P}}-O-(CH_2)_q-NH_2,$$

3.7 inositol,
3.8 inositol phosphate,
3.9 a phosphate group bearing a phenyl, benzyl, or propylnitrile moiety, or
3.10 —$(CH_2)_x$—CN, and
q is an integer from 2 to 4 and
x is an integer from 1 to 4, except
$R^6$ cannot be —O— when $R^7$ is hydrogen and
p is 2, and
$R^6$ cannot be —O—CO—O— when $R^7$ is hydrogen, $R^1$ is:
a) —($C_1$–$C_4$)-alkyl, or
b) =O, $R^2$ is:
a) a sulfhydryl protecting group,
b) ($C_1$–$C_3$)-alkyl, or
c) a hydrogen atom, $R^3$ and $R^4$ independently of one another are:
a) a hydrogen atom, or
b) methyl, and w is an integer 1 or 2, or a stereoisomeric form, or a dimer of the peptide of formula I with cystine as the dimerization component, or a physiologically acceptable salt of the peptide of formula I.

2. A peptide as claimed in claim 1, wherein:

G is an amino acid residue substituted by acetyl, penicillinamine, 2-(thien-2-yl)-glycine, Tyr, Ash, Phe, Trp, Nal, D-Tyr, or D-Asn, D is Asp, Asn, D-Asp, D-Asn, Tyr, D-Tyr, glucosamine or a covalent bond, E is:
a) —NH—$(CH_2)_n$—$NR^5_2$, in which each $R^5$ is identical or different and is a moiety selected from the group consisting of
1) a hydrogen atom,
2) glucose,
3) gluconic acid, 4) galactonic acid,
5) mannonic acid,
6) glucosamine,
7) mannose,
8) fructose,
9) galactose,
10) dimannose, and
11) trimannose, and
n is an integer from 0 to 4, except n cannot be 1 when $R^5$ is hydrogen, or
b) —NH—$(CH_2)_p$—$R^6$—$R^7$, in which $R^6$ is:
1) —O—,
2) —O—CO—O—,

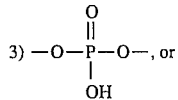

3) —O—P(=O)(OH)—O—, or

4) —NH—CO—O—,
$R^7$ is:
1) a hydrogen atom, or
2) selected from the group consisting of
   a) glucose,
   b) gluconic acid,
   c) galactonic acid,
   d) mannonic acid,
   e) glucosamine,
   f) mannose,
   g) fructose,
   h) galactose,
   i) dimannose, and
   j) trimannose, and
p is an integer from 2 to 4, except
$R^6$ cannot be —O— when $R^7$ is hydrogen and p is 2, and
$R^6$ cannot be —O—CO—O— when $R^7$ is hydrogen,
$R^1$ is:
   a) =O, or
   b) methyl,
$R^2$ is:
   a) a hydrogen atom, or
   b) methyl, and
w is the integer 1 or 2,
a stereoisomeric form or a physiologically acceptable salt of the peptide of formula I.

3. A peptide as claimed in claim 1, wherein
   G is a residue selected from the group consisting of Tyr, Asn, D-Tyr, D-Asn, 2-(thien-2-yl)glycine, 3-(thien-2-yl)alanine and Phe,
   D is a residue selected from the group consisting of Asn, Tyr, D-Asn and D-Tyr,
   E is ethylenediamine,
   W is 1 or 2,
   $R^1$ is =O, and
   $R^2$ is a hydrogen atom or methyl,
a stereoisomeric form or a physiologically acceptable salt of the peptide of formula I.

4. A peptide as claimed in claim 1, wherein
   G is a residue selected from the group consisting of Tyr, D-Tyr and Asn,
   D represents a covalent bond, or an amino acid residue selected from the group consisting of L-asparaginyl and D-asparaginyl,
   E is:

a) ethylenediamine, or
b) —NH—$(CH_2)_p$—$R^6$—$R^7$, in which $R^6$ is:
   1) —O—, or

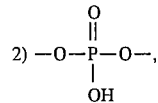

2) —O—P(=O)(OH)—O—, and $R^7$ is:
   1) a hydrogen atom,
   2) mannose, or
   3) mannose monosubstituted or tetrasubstituted independently of one another by:
      3.1 methyl,
      3.2 mannose,
      3.3 dimannose,
      3.4 galactose, or
      3.5 digalactose except
$R^6$ cannot be —O— when $R^7$ is hydrogen and p is 2,
$R^1$ is =O,
$R^2$, $R^3$ and $R^4$ are all hydrogen atoms and
w is 1,
a stereoisomeric form or a physiologically acceptable salt of the peptide of formula I.

5. A pharmaceutical formulation for the treatment of diabetes mellitus comprising at least one peptide of formula I as claimed in claim 1 wherein said peptide is in dissolved, amorphous or crystalline form, together with a pharmaceutically acceptable carrier.

6. A pharmaceutical formulation as claimed in claim 5, further comprising insulin or an insulin analog.

7. A process for the preparation of a pharmaceutical formulation for the treatment of diabetes mellitus, said formulation comprising at least one peptide of formula I as claimed in claim 1, wherein said peptide is in dissolved, amorphous or crystalline form, together with a pharmaceutically acceptable carrier,
   wherein said process comprises combining at least one peptide of formula I with a pharmaceutically and physiologically acceptable excipient, additive, or adjunct.

8. The process as claimed in claim 7, further comprising at least one insulin or insulin analog.

9. A method of treating diabetes mellitus or insulin-independent diabetes comprising administering to a patient having diabetes mellitus or insulin-independent diabetes at least one peptide of the formula I:

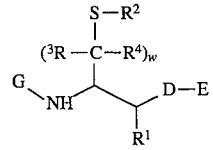

(I)

in which
G is:
   a) a hydrogen atom,
   b) an amino acid residue, or
   c) an amino acid residue monosubstituted or polysubstituted by:
      1) —CO—$(C_1$–$C_8)$-alkyl, linear or branched, or
      2) an amino acid protecting group,
D is:
   a) an amino acid residue,
   b) a phosphoamino acid residue, c) a monosaccharide residue, or
d) a covalent bond, E is:
a) —NR—(CH$_2$)$_n$—NR$^5$$_2$, in which each R$^5$ is identical or different and is a moiety selected from the group consisting of
  1) a hydrogen atom,
  2) 1 to 6 monosaccharide residues, and
  3) 1 to 6 monosaccharide residues monosubstituted or polysubstituted independently of one another by:
    3.1 methyl,
    3.2 a monosaccharide residue,
    3.3 a disaccharide residue,

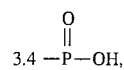
3.4

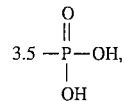
3.5

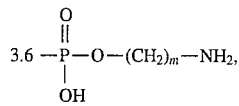
3.6

3.7 inositol,
  3.8 inositol phosphate, or
  3.9 a phosphate group bearing a phenyl, benzyl, or propylnitrile moiety,
  n is an integer from 0 to 6, except
  n cannot be 1 when R$^5$ is hydrogen, and
  m is an integer from 0 to 4,
b) a glycerol residue, or
c) —NH—(CH$_2$)$_p$—R$^6$—R$^7$, in which p is 2 to 4, R$^6$ is:
1) —O—,

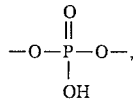
2)

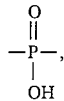
3)

4) —NH—CO—O—,
5) —S— or
6) —O—CO—O—,

R$^7$ is:
1) a hydrogen atom,
2) 1 to 6 monosaccharide residues, or
3) 1 to 6 monosaccharide residues monosubstituted or polysubstituted independently of one another by:
  3.1 methyl,
  3.2 a monosaccharide residue,
  3.3 a disaccharide residue,

3.4

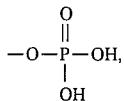
3.5

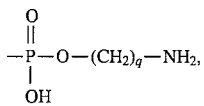
3.6

3.7 inositol,
  3.8 inositol phosphate,
  3.9 a phosphate group bearing a phenyl, benzyl, or propylnitrile moiety, or
  3.10 —(CH$_2$)$_x$—CN, and
  q is an integer from 2 to 4 and
  x is an integer from 1 to 4, except R6 cannot be —O—CO—O— when R7 is hydrogen, R$^1$ is:
a) —(C$_1$-C$_4$)-alkyl, or
b) =O, R$^2$ is:
a) a sulfhydryl protecting group,
b) (C$_1$-C$_3$)-alkyl, or
c) a hydrogen atom, R$^3$ and R$^4$ independently of one another are:
a) a hydrogen atom, or
b) methyl, and w is an integer 1 or 2, or a stereoisomeric form, or a dimer of the peptide of formula I with cystine as the dimerization component, or a physiologically acceptable salt of the peptide of formula I.

* * * * *

UNITED STATES PATENT AND TRADEMARK OFFICE
CERTIFICATE OF CORRECTION

PATENT NO.    : 5,622,934
DATED         : April 22, 1997
INVENTOR(S)   : Wendelin FRICK et al.

It is certified that error appears in the above-indentified patent and that said Letters Patent is hereby corrected as shown below:

Title page, item [75], "Inventors", line 1, "Frankfur am Main" should read --Franfurt am Main--.

Title page, item [57], "Abstract", line 3, "add" should read --acid--, line 13, after "$R^6$ is 0", insert --,--.

Claim 4, column 18, line 22, after "hydrogen atoms" insert --,--.

Claim 5, column 18, line 29, after "claim 1" insert --,--.

Signed and Sealed this

Nineteenth Day of May, 1998

Attest:

BRUCE LEHMAN

*Attesting Officer*                *Commissioner of Patents and Trademarks*